(12) United States Patent
de Villiers et al.

(10) Patent No.: US 11,707,360 B2
(45) Date of Patent: Jul. 25, 2023

(54) INTERVERTEBRAL PROSTHESIS

(71) Applicant: Simplify Medical Pty Ltd, Melbourne (AU)

(72) Inventors: Malan de Villiers, Wapadrand (ZA); Ulrich Reinhard Hahnle, Saxonwold (ZA)

(73) Assignee: Simplify Medical Pty Ltd, Melbourne (AU)

( * ) Notice: Subject to any disclaimer, the term of this patent is extended or adjusted under 35 U.S.C. 154(b) by 9 days.

(21) Appl. No.: 17/565,858

(22) Filed: Dec. 30, 2021

(65) Prior Publication Data

US 2022/0202590 A1 Jun. 30, 2022

Related U.S. Application Data

(60) Division of application No. 16/108,773, filed on Aug. 22, 2018, now Pat. No. 11,285,013, which is a
(Continued)

(30) Foreign Application Priority Data

Sep. 19, 2002 (ZA) ................ 200207517A

(51) Int. Cl.
*A61F 2/44* (2006.01)
*A61F 2/46* (2006.01)
*A61F 2/30* (2006.01)

(52) U.S. Cl.
CPC ........ *A61F 2/4425* (2013.01); *A61F 2/30771* (2013.01); *A61F 2/4611* (2013.01);
(Continued)

(58) Field of Classification Search
CPC .................. A61F 2/4425; A61F 2002/443
See application file for complete search history.

(56) References Cited

U.S. PATENT DOCUMENTS 3,486,505 A 12/1969 Gordon
4,566,466 A 1/1986 Ripple et al.
(Continued)

FOREIGN PATENT DOCUMENTS

DE 3023353 A1 4/1981
EP 0333990 A2 9/1989
(Continued)

OTHER PUBLICATIONS

Buttner-Janz, The Development of the Artificial Disc. Introduction, pp. 1-18, Library of Congress Catalogue No. 92-75582, ISBN 0-9635430-0-8 (1989).
(Continued)

*Primary Examiner* — Olivia C Chang
(74) *Attorney, Agent, or Firm* — Hoffman Warnick LLC

(57) ABSTRACT

An intervertebral prosthesis for insertion between adjacent vertebrae includes upper and lower prosthesis plates locatable against respective vertebrae and having opposing concavely curved recesses therein, and a core located between the plates. The core has opposed, convexly curved surfaces received in the recesses of the plates to allow the plates to slide in articulated manner over the core. The opposed surfaces of the core and the recesses of the plates have cooperating spherical curvatures. The recess of each plate surrounds a locating peg projecting centrally from the base of the recess and is bounded by an annular rim, such that the annular rims of the plates are arranged to contact one another at a predetermined limit of sliding movement of the plates over the core. The peg locates loosely in an opening located centrally in a curved surface of the core, whereby the plates can slide over the core in all directions while the peg holds the core captive.

20 Claims, 4 Drawing Sheets

Related U.S. Application Data continuation of application No. 15/458,913, filed on Mar. 14, 2017, now Pat. No. 10,166,113, which is a continuation of application No. 15/284,344, filed on Oct. 3, 2016, now Pat. No. 9,839,525, which is a continuation of application No. 11/982,420, filed on Oct. 31, 2007, now abandoned, which is a continuation of application No. 11/084,224, filed on Mar. 18, 2005, now Pat. No. 7,531,001, which is a continuation-in-part of application No. PCT/IB03/01529, filed on Apr. 24, 2003.

(52) U.S. Cl.
CPC . *A61F 2002/302* (2013.01); *A61F 2002/3008* (2013.01); *A61F 2002/30332* (2013.01); *A61F 2002/30364* (2013.01); *A61F 2002/30369* (2013.01); *A61F 2002/30528* (2013.01); *A61F 2002/30662* (2013.01); *A61F 2002/30785* (2013.01); *A61F 2002/30822* (2013.01); *A61F 2002/30841* (2013.01); *A61F 2002/30884* (2013.01); *A61F 2002/30899* (2013.01); *A61F 2002/30904* (2013.01); *A61F 2002/443* (2013.01); *A61F 2220/0016* (2013.01); *A61F 2220/0025* (2013.01); *A61F 2220/0033* (2013.01); *A61F 2230/0065* (2013.01); *A61F 2250/0098* (2013.01); *A61F 2310/00017* (2013.01); *A61F 2310/00029* (2013.01); *A61F 2310/0088* (2013.01); *A61F 2310/00179* (2013.01)

(56) References Cited

U.S. PATENT DOCUMENTS

| | | |
|---|---|---|
| 4,759,766 A | 7/1988 | Buettner-Janz et al. |
| 4,759,769 A | 7/1988 | Hedman et al. |
| 4,834,757 A | 5/1989 | Brantigan |
| 4,863,477 A | 9/1989 | Monson |
| 4,946,378 A | 8/1990 | Hirayama et al. |
| 4,997,432 A | 3/1991 | Keller et al. |
| 5,035,716 A | 7/1991 | Downey |
| 5,057,108 A | 10/1991 | Shetty et al. |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |
| 5,282,661 A | 2/1994 | Arnberger |
| 5,282,861 A | 2/1994 | Kaplan |
| 5,306,308 A | 4/1994 | Gross et al. |
| 5,314,477 A | 5/1994 | Marnay |
| 5,370,697 A | 12/1994 | Baumgartner et al. |
| 5,401,269 A | 3/1995 | Buettner-Janz et al. |
| 5,415,704 A | 5/1995 | Davidson |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Büttner-Janz |
| 5,674,296 A | 10/1997 | Bryan et al. |
| 5,676,701 A | 10/1997 | Yuan et al. |
| 5,676,702 A | 10/1997 | Ratron |
| 5,702,450 A | 12/1997 | Bisserie |
| 5,709,683 A | 1/1998 | Bagby |
| 5,728,159 A | 3/1998 | Stroever et al. |
| 5,797,909 A | 8/1998 | Michelson |
| 5,824,094 A | 10/1998 | Serhan et al. |
| 5,865,846 A | 2/1999 | Bryan et al. |
| 5,888,226 A | 3/1999 | Rogozinski |
| 5,899,901 A | 5/1999 | Middleton |
| 5,899,911 A | 5/1999 | Carter |
| 5,928,284 A | 7/1999 | Mehdizadeh |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,763 A | 3/2000 | Shelokov |
| 6,080,155 A | 6/2000 | Michelson |
| 6,083,228 A | 7/2000 | Michelson |
| 6,096,038 A | 8/2000 | Michelson |
| 6,132,465 A | 10/2000 | Ray et al. |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,176,881 B1 | 1/2001 | Schaer et al. |
| 6,224,595 B1 | 5/2001 | Michelson |
| 6,235,030 B1 | 5/2001 | Zucherman et al. |
| 6,261,296 B1 | 7/2001 | Aebi et al. |
| 6,264,695 B1 | 7/2001 | Stoy |
| 6,315,797 B1 | 11/2001 | Middleton |
| 6,322,567 B1 | 11/2001 | Mittelstadt et al. |
| 6,348,071 B1 | 2/2002 | Steffee et al. |
| 6,368,350 B1 | 4/2002 | Erickson et al. |
| 6,395,032 B1 | 5/2002 | Gauchet |
| 6,416,551 B1 | 7/2002 | Keller |
| 6,436,098 B1 | 8/2002 | Michelson |
| 6,440,139 B2 | 8/2002 | Michelson |
| 6,447,548 B1 | 9/2002 | Ralph et al. |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |
| 6,562,047 B2 | 5/2003 | Ralph et al. |
| 6,562,074 B2 | 5/2003 | Gerbec et al. |
| 6,565,574 B2 | 5/2003 | Michelson |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 | 7/2003 | Fuss et al. |
| 6,607,558 B2 | 8/2003 | Kuras |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,652,533 B2 | 11/2003 | O'Neil |
| 6,660,038 B2 | 12/2003 | Boyer et al. |
| 6,666,866 B2 | 12/2003 | Martz et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,825 B2 | 3/2004 | Aebi et al. |
| 6,719,794 B2 | 4/2004 | Gerber et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,728,720 B1 | 4/2004 | Lenzie |
| 6,733,532 B1 | 5/2004 | Gauchet et al. |
| 6,740,118 B2 | 5/2004 | Eisermann et al. |
| 6,740,119 B2 | 5/2004 | Ralph et al. |
| 6,752,832 B2 | 6/2004 | Neumann |
| 6,770,095 B2 | 8/2004 | Grinberg et al. |
| 6,814,737 B2 | 11/2004 | Cauthen |
| 6,827,740 B1 | 12/2004 | Michelson |
| 6,852,126 B2 | 2/2005 | Ahlgren |
| 6,875,213 B2 | 4/2005 | Michelson |
| 6,896,680 B2 | 5/2005 | Michelson |
| 6,936,071 B1 | 8/2005 | Marnay et al. |
| 6,936,132 B2 | 8/2005 | Topolnitsky |
| 6,966,929 B2 | 11/2005 | Mitchell |

(56) References Cited

U.S. PATENT DOCUMENTS

| | | | |
|---|---|---|---|
| 6,986,788 B2 | 1/2006 | Paul et al. |
| 6,994,727 B2 | 2/2006 | Khandkar et al. |
| 7,025,787 B2 | 4/2006 | Bryan et al. |
| 7,056,344 B2 | 6/2006 | Huppert et al. |
| 7,060,073 B2 | 6/2006 | Frey et al. |
| 7,169,182 B2 | 1/2007 | Errico et al. |
| 7,172,784 B2 | 2/2007 | Prabhasankar et al. |
| 7,179,294 B2 | 2/2007 | Eisermann et al. |
| 7,182,784 B2 | 2/2007 | Evans et al. |
| 7,270,679 B2 | 9/2007 | Istephanous et al. |
| 7,303,582 B2 | 12/2007 | Brady et al. |
| 7,303,583 B1 | 12/2007 | Schaer et al. |
| 7,326,250 B2 | 2/2008 | Beaurain et al. |
| 7,442,211 B2 | 10/2008 | De et al. |
| 7,531,001 B2 | 5/2009 | De et al. |
| 7,575,599 B2 | 8/2009 | Villiers et al. |
| 7,585,326 B2 | 9/2009 | De et al. |
| 7,637,913 B2 | 12/2009 | De et al. |
| 7,682,396 B2 | 3/2010 | Beaurain et al. |
| 7,731,754 B2 | 6/2010 | De et al. |
| 8,262,732 B2 | 9/2012 | De et al. |
| 9,839,525 B2 | 12/2017 | De et al. |
| 10,166,113 B2 | 1/2019 | Villiers et al. |
| 2001/0016773 A1 | 8/2001 | Serhan et al. |
| 2001/0027343 A1 | 10/2001 | Keller |
| 2001/0029377 A1 | 10/2001 | Aebi et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0123753 A1 | 9/2002 | Michelson |
| 2002/0128715 A1 | 9/2002 | Bryan et al. |
| 2002/0177897 A1 | 11/2002 | Michelson |
| 2002/0198532 A1 | 12/2002 | Michelson |
| 2003/0009224 A1 | 1/2003 | Kuras |
| 2003/0028249 A1 | 2/2003 | Baccelli et al. |
| 2003/0045939 A1 | 3/2003 | Casutt |
| 2003/0074076 A1 | 4/2003 | Ferree et al. |
| 2003/0100951 A1 | 5/2003 | Serhan et al. |
| 2003/0130662 A1 | 7/2003 | Michelson |
| 2003/0135277 A1 | 7/2003 | Bryan et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0208273 A1 | 11/2003 | Eisermann et al. |
| 2003/0229358 A1 | 12/2003 | Errico et al. |
| 2004/0002716 A1 | 1/2004 | Furutsu |
| 2004/0002761 A1 | 1/2004 | Rogers et al. |
| 2004/0024407 A1 | 2/2004 | Ralph et al. |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0059318 A1 | 3/2004 | Zhang et al. |
| 2004/0073307 A1 | 4/2004 | Keller |
| 2004/0073312 A1 | 4/2004 | Eisermann et al. |
| 2004/0098131 A1 | 5/2004 | Bryan et al. |
| 2004/0143270 A1 | 7/2004 | Zucherman et al. |
| 2004/0176843 A1 | 9/2004 | Zubok et al. |
| 2004/0215342 A1 | 10/2004 | Suddaby |
| 2004/0243240 A1 | 12/2004 | Beaurain ............... A61F 2/4425 623/17.14 |
| 2005/0021145 A1 | 1/2005 | De et al. |
| 2005/0021146 A1 | 1/2005 | De et al. |
| 2005/0043800 A1 | 2/2005 | Paul et al. |
| 2005/0085917 A1 | 4/2005 | Marnay et al. |
| 2005/0107881 A1 | 5/2005 | Alleyne et al. |
| 2005/0149189 A1 | 7/2005 | Mokhtar et al. |
| 2005/0192586 A1 | 9/2005 | Zucherman et al. |
| 2005/0192670 A1 | 9/2005 | Zubok et al. |
| 2005/0197706 A1 | 9/2005 | Hovorka et al. |
| 2005/0251262 A1 | 11/2005 | De et al. |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004453 A1 | 1/2006 | Bartish, Jr. et al. |
| 2006/0025862 A1 | 2/2006 | Villiers et al. |
| 2006/0029186 A1 | 2/2006 | De et al. |
| 2006/0030857 A1 | 2/2006 | De et al. |
| 2006/0030862 A1 | 2/2006 | De et al. |
| 2006/0036325 A1 | 2/2006 | Paul et al. |
| 2006/0041313 A1 | 2/2006 | Allard et al. |
| 2006/0069439 A1 | 3/2006 | Zucherman et al. |
| 2006/0178744 A1 | 8/2006 | De et al. |
| 2006/0293754 A1 | 12/2006 | Devilliers et al. |
| 2007/0061011 A1 | 3/2007 | De et al. |
| 2007/0282449 A1 | 12/2007 | De et al. |
| 2008/0051900 A1 | 2/2008 | De et al. |
| 2008/0051901 A1 | 2/2008 | De et al. |
| 2008/0125864 A1 | 5/2008 | De et al. |
| 2008/0133011 A1 | 6/2008 | De et al. |
| 2008/0133013 A1 | 6/2008 | Duggal et al. |
| 2008/0154301 A1 | 6/2008 | De et al. |
| 2008/0154382 A1 | 6/2008 | De et al. |
| 2008/0215155 A1 | 9/2008 | De et al. |
| 2008/0221696 A1 | 9/2008 | De et al. |
| 2008/0228274 A1 | 9/2008 | De et al. |
| 2008/0228277 A1 | 9/2008 | De et al. |
| 2008/0294259 A1 | 11/2008 | De et al. |
| 2009/0043391 A1 | 2/2009 | De et al. |
| 2009/0105833 A1 | 4/2009 | Hovda et al. |
| 2009/0105834 A1 | 4/2009 | Hovda et al. |
| 2009/0105835 A1 | 4/2009 | Hovda et al. |
| 2009/0205188 A1 | 8/2009 | De et al. |
| 2009/0210060 A1 | 8/2009 | De et al. |
| 2009/0222101 A1 | 9/2009 | De et al. |
| 2009/0276051 A1 | 11/2009 | Arramon et al. |
| 2010/0004746 A1 | 1/2010 | Arramon |
| 2010/0016972 A1 | 1/2010 | Jansen et al. |
| 2010/0016973 A1 | 1/2010 | De et al. |
| 2010/0049040 A1 | 2/2010 | De et al. |
| 2010/0069976 A1 | 3/2010 | De et al. |
| 2010/0076558 A1 | 3/2010 | De et al. |
| 2010/0087868 A1 | 4/2010 | Barr et al. |
| 2010/0179419 A1 | 7/2010 | De et al. |
| 2017/0020681 A1 | 1/2017 | Villiers et al. |
| 2018/0071112 A1 | 3/2018 | Villiers et al. |

FOREIGN PATENT DOCUMENTS

| | | |
|---|---|---|
| EP | 0333990 A3 | 5/1990 |
| EP | 0560140 A1 | 9/1993 |
| EP | 0560141 A1 | 9/1993 |
| EP | 0591712 A1 | 4/1994 |
| EP | 0820740 A1 | 1/1998 |
| EP | 1142544 A1 | 10/2001 |
| EP | 1153582 A2 | 11/2001 |
| EP | 1153582 A3 | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1417940 A1 | 5/2004 |
| FR | 2803741 A1 | 7/2001 |
| JP | S61122859 A | 6/1986 |
| JP | H01136655 A | 5/1989 |
| JP | 06007391 | 1/1994 |
| JP | H067391 A | 1/1994 |
| JP | 2002521090 A | 7/2002 |
| JP | 2003508119 A | 3/2003 |
| WO | WO-9920209 A1 | 4/1999 |
| WO | WO-9930651 A1 | 6/1999 |
| WO | WO-0004851 A1 | 2/2000 |
| WO | WO-0035384 A1 | 6/2000 |
| WO | WO-0042954 A2 | 7/2000 |
| WO | WO-0042954 A3 | 11/2000 |
| WO | WO-0101893 A1 | 1/2001 |
| WO | WO-0115637 A1 | 3/2001 |

(56) References Cited

FOREIGN PATENT DOCUMENTS

| WO | WO-2004026187 A1 | 4/2004 |
|---|---|---|
| WO | WO-2005053580 A1 | 6/2005 |
| ZA | 200603171 | 9/2007 |

OTHER PUBLICATIONS

European search report dated Dec. 10, 2008 for EP 08163926.2.
Hellier; et al., Wear Studies for Development of an Intervertebral Disc Prosthesis. Spine, vol. 17 No. 6 Supplement pp. 86-96 (1992).
International search report dated Jul. 18, 2003 for PCT/IB2003/001529.
International search report dated Jul. 21, 2005 for PCT/US2005/026160.
International search report dated Jul. 21, 2007 for PCT/US2006/002263.
Lee, et al. Impact Response of the Intervertebral Disc in a Finite-Element Model. Spine. 2000; 25(19):2431-2439.
Lehuec, et al. Shock Absorption in Lumber Disc Prosthesis. Journal of Spinal Disorders & Techniques. 2003; 16(4):346-351.
Notice of Allowability dated Oct. 17, 2017 for U.S. Appl. No. 14/744,910.
Notice of allowance dated Feb. 26, 2009 for U.S. Appl. No. 11/084,224.
"Notice of Allowance dated Oct. 10, 2017 for U.S. Appl. No. 15/284,344".
Office action dated Jan. 16, 2008 for U.S. Appl. No. 11/084,224.
Office action dated Jan. 19, 2011 for U.S. Appl. No. 12/731,993.
Office action dated Jan. 23, 2007 for U.S. Appl. No. 11/084,224.
Office action dated Feb. 15, 2017 for U.S. Appl. No. 15/284,344.
Office action dated Feb. 25, 2011 for U.S. Appl. No. 12/129,868.
Office action dated Mar. 15, 2010 for U.S. Appl. No. 12/129,868.
"Office action dated Apr. 4, 2017 for U.S. Appl. No. 15/284,344."
Office action dated Apr. 10, 2008 for US Application No. 11/468,618.
Office action dated Apr. 24, 2009 for U.S. Appl. No. 11/982,420.
Office action dated Apr. 27, 2006 for U.S. Appl. No. 11/084,224.
Office action dated Apr. 29, 2010 for U.S. Appl. No. 11/982,431.
Office action dated May 1, 2009 for U.S. Appl. No. 11/468,601.
Office action dated May 1, 2009 for U.S. Appl. No. 11/468,618.
Office action dated May 8, 2007 for U.S. Appl. No. 11/084,224.
Office action dated May 23, 2008 for U.S. Appl. No. 11/084,224.
"Office action dated Jun. 1, 2017 for U.S. Appl. No. 15/458,913."
"Office action dated Jun. 21, 2017 for U.S. Appl. No. 15/284,344".
Office action dated Jul. 1, 2011 for U.S. Appl. No. 12/731,993.
Office action dated Jul. 10, 2009 for U.S. Appl. No. 11/982,431.
Office action dated Jul. 10, 2013 for U.S. Appl. No. 11/982,420.
Office action dated Jul. 11, 2008 for U.S. Appl. No. 11/468,601.
Office action dated Aug. 21, 2009 for U.S. Appl. No. 11/982,420.
Office action dated Aug. 23, 2011 for U.S. Appl. No. 12/129,868.
Office action dated Aug. 31, 2010 for U.S. Appl. No. 11/468,601.
Office action dated Oct. 8, 2009 for U.S. Appl. No. 11/468,601.
Office action dated Oct. 19, 2010 for U.S. Appl. No. 12/129,868.
Office action dated Oct. 26, 2009 for U.S. Appl. No. 11/982,431.
Office action dated Oct. 31, 2011 for U.S. Appl. No. 11/982,420.
Office action dated Nov. 6, 2009 for U.S. Appl. No. 11/982,420.
Office action dated Nov. 21, 2008 for U.S. Appl. No. 11/468,601.
Office action dated Dec. 5, 2008 for U.S. Appl. No. 11/084,224.
Office action dated Dec. 15, 2008 for U.S. Appl. No. 11/982,431.
Office action dated Dec. 26, 2007 for U.S. Appl. No. 11/468,601.
U.S. Appl. No. 15/458,913 Notice of Allowance dated May 24, 2018.
U.S. Appl. No. 60/546,027, filed Feb. 19, 2004.
"U.S. Appl. No. 15/458,913 Notice of Allowance dated Jan. 31, 2018".
Co-pending U.S. Appl. No. 15/458,913, filed Mar. 14, 2017.

INTERVERTEBRAL PROSTHESIS

CROSS-REFERENCES TO RELATED APPLICATIONS

The present application is a divisional of U.S. patent application Ser. No. 16/108,773, now U.S. Pat. No., which is a continuation of U.S. patent application Ser. No. 15/458,913, filed Mar. 14, 2017, now U.S. Pat. No. 10,166,113, which is a continuation of U.S. patent application Ser. No. 15/284,344, filed Oct. 3, 2016, which is a continuation of U.S. patent application Ser. No. 11/982,420, filed Oct. 31, 2007, which is a continuation of Ser. No. 11/084,224 filed Mar. 18, 2005, now U.S. Pat. No. 7,531,001, which is a continuation-in-part of PCT/IB2003/001529 filed on Apr. 24, 2003, designating the United States, which claimed priority from South African application 2002/7517 filed on Sep. 19, 2002, the full disclosures of which are incorporated herein by reference.

BACKGROUND OF THE INVENTION

1. Field of the Invention

This invention relates to an intervertebral prosthesis.

In the event of damage to a spinal disc it is known practice to implant an intervertebral prosthesis surgically to replace the damaged organ. Several types of prosthesis for this purpose are known and in common use.

One type of known intervertebral prosthesis is sold by Waldemar Link GmbH & Co under the trade mark LINK® SB Charite. This prosthesis includes upper and lower prosthesis plates which locate against and engage the adjacent vertebral bodies, and a low friction core between the plates. The core has upper and lower convexly curved surfaces and the plates have corresponding, concavely curved recesses which cooperate with the curved surfaces of the core. This allows the plates to slide over the core to allow required spinal movements to take place. The curved recesses in the plates are surrounded by annular ridges which locate, at the limit of sliding movement of the plates over the core, in opposing peripheral channels surrounding the curved surfaces of the core.

This type of configuration is also described in EP 0 560 140 and EP 0 560 141 (both Waldemar Link GmbH & Co). However a drawback of such configurations is that the provision of the peripheral ribs and channels limits the areas available for bearing and sliding contact between the plates and core, and accordingly the loads which can be transmitted by the prosthesis. As a result of the relatively small bearing areas, it is believed that at least the core will be subject to rapid wear and have a relatively short life-span.

EP 0 560 141 also describes one alternative arrangement in which the curved surfaces of the core carry opposing, elongate keys that locate in elongate grooves in the plates and another alternative arrangement in which the plates have opposing elongate keys that locate in elongate grooves in the opposite curved surfaces of the core. These key and groove arrangements allow the plates to slide freely over the core, within the limits of the length of the grooves, in one plane only. Although allowance is made for some lateral play of the keys in the grooves, very little sliding movement of the plates over the core can take place in the orthogonal vertical plane, and this is considered to be a serious drawback of this design.

2. Description of the Background Art

European Patent Publications EP 0 560 140 and EP 0 560 141 have been discussed above. U.S. Patent Publications US2002/0035400 and US2002/0128715 describe intervertebral prostheses with center-posts received in passages in a core. The core possesses an annular flange structure engaged by extensions on the plates.

BRIEF SUMMARY OF THE INVENTION

According to the invention there is provided an intervertebral prosthesis for insertion between adjacent vertebrae, the prosthesis comprising upper and lower prosthesis plates locatable against the respective vertebrae and having opposing, concavely curved recesses therein and a core located between the plates, the core having opposed, convexly curved surfaces received in the recesses of the plates to allow the plates to slide in articulated manner over the core, characterized in that:

the opposed surfaces of the core and the recesses of the plates have cooperating spherical curvatures, the recess of a plate surrounds a locating peg projecting centrally from the base of the recess, and the peg locates loosely in an opening located centrally in a curved surface of the core, whereby the plates can slide over the core in all directions while the peg holds the core captive.

In some embodiments, only one of the plates, typically the operatively lower plate, includes a peg. In other embodiments, both plates include pegs, the pegs opposing one another and locating loosely in respective openings located centrally in the opposed curved surfaces of the core. In each embodiment it is preferred that each peg and the opening in which it locates are conical in shape.

According to another aspect of the invention there is provided a prosthesis plate for use in a prosthesis as summarized above, the prosthesis plate having a coarse surface locatable against a vertebra, an oppositely facing concavely curved surface which is complemental in shape to a convexly curved surface of a core of the prosthesis, characterized in the concavely curved surface of the plate has a spherical curvature and in that the plate includes a conical locating peg extending centrally from the concavely curved surface, the peg being locatable loosely in a central opening in the convexly curved surface of the core.

According to yet another aspect of the invention there is provided a core for use in the prosthesis, the core comprising a one piece plastics body having operatively upper and lower curved surfaces, characterized in that the curved surfaces of the body are spherically curved and at least one of the surfaces has a central, conical opening therein dimensioned to receive a conical locating peg of a prosthesis plate loosely.

Other features of the invention are set forth in the appended claims.

BRIEF DESCRIPTION OF THE DRAWINGS

The invention will now be described in more detail, by way of example only, with reference to the accompanying drawings in which.

DETAILED DESCRIPTION OF THE INVENTION

Figure 1:
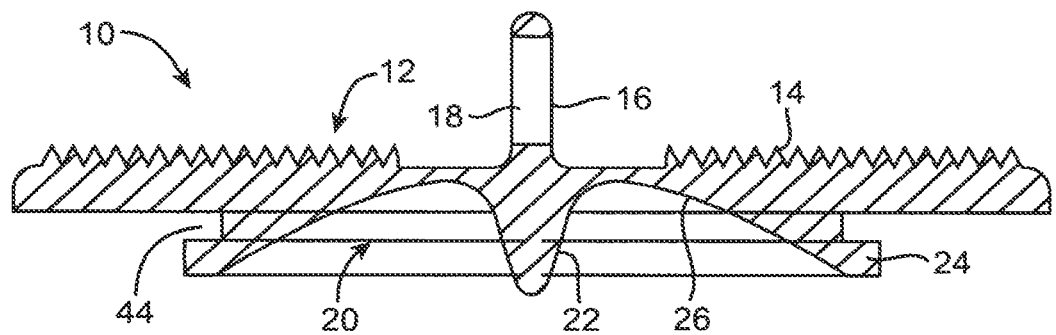
FIG. 1 shows a cross-sectional view of a prosthesis plate used in a prosthesis according to the invention.
Figure 2:
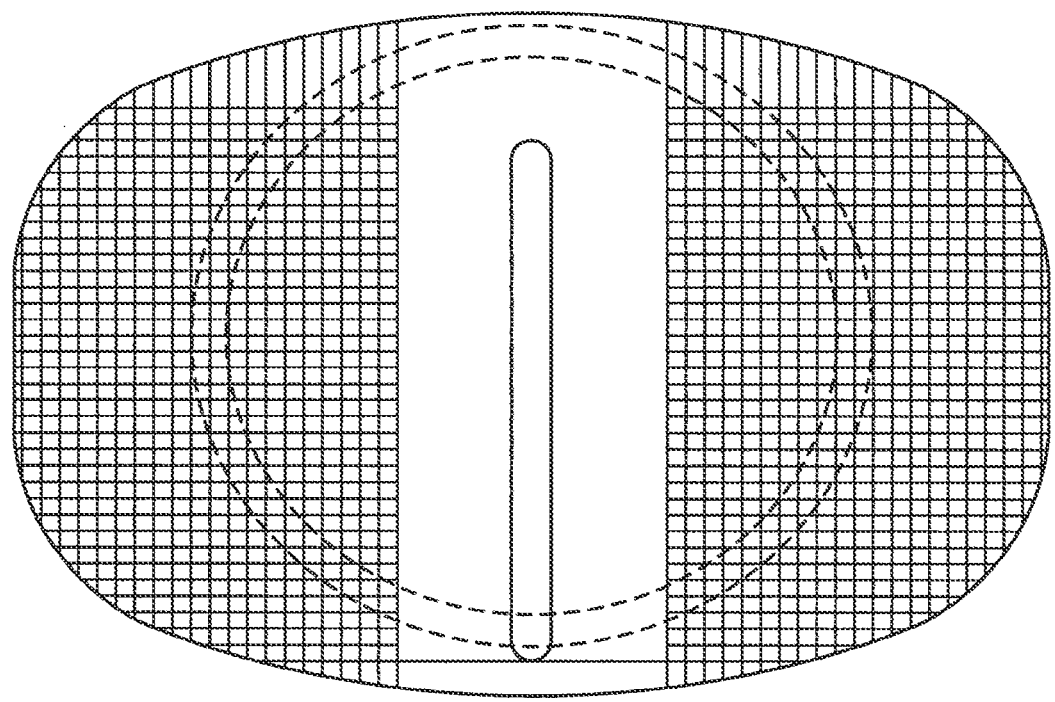
FIG. 2 shows a plan view of the prosthesis plate seen in FIG. 1.

The prosthesis plate 10 seen in FIGS. 1 and 2 may be formed from titanium, typically being formed in one piece of grade 5 titanium. Other suitable materials include titanium nitrides, cobalt chrome alloys, and ceramics. The prosthesis plate includes a major surface 12 which is machined to a coarse, serrated finish 14. Projecting from the surface 12 is an elongate fin 16 pierced by transverse holes 18. The opposite surface of the plate 10 is formed with a recess 20 surrounding a projecting conical peg 22 of round cross-section at the center of the recess. The recess is bounded by an annular rim 24. The surface 26 of the recess is concavely, spherically curved and has a titanium nitride finish.

Figure 4:
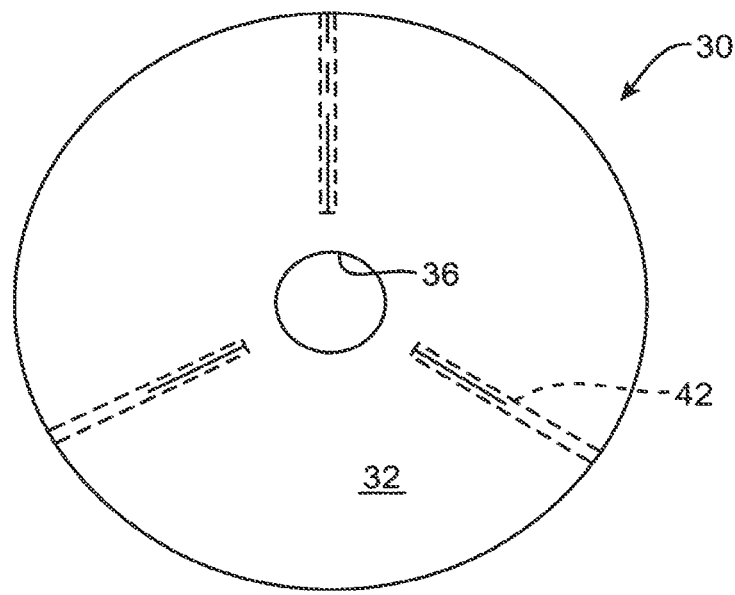
FIG. 4 shows a plan view of the core seen in FIG. 3.
Figure 5:
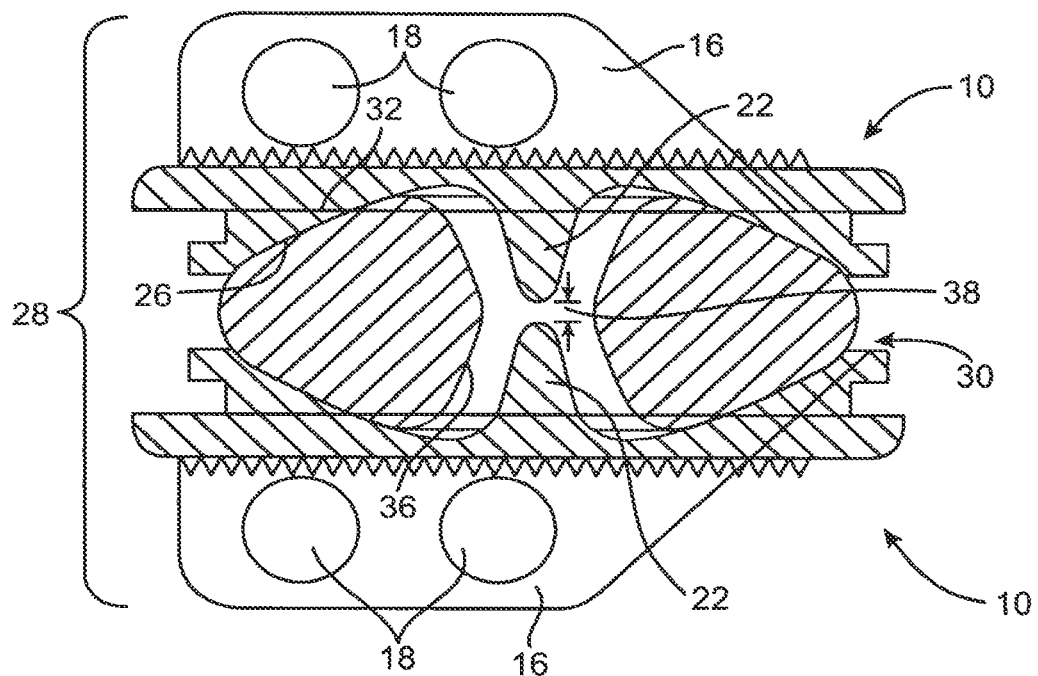
FIG. 5 shows a cross-sectional view of an intervertebral prosthesis according to a first embodiment of the invention in a neutral condition before articulation has taken place.
Figure 6:
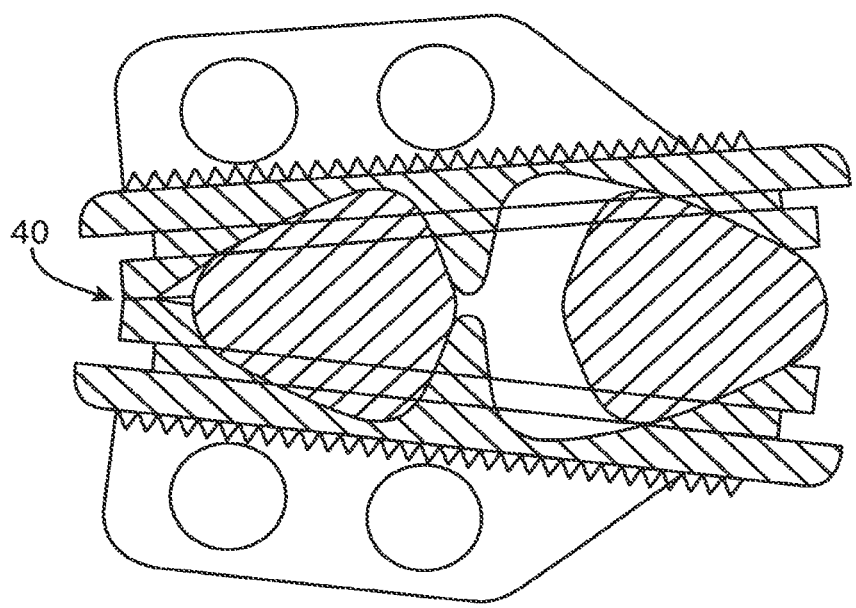
FIG. 6 shows the prosthesis of FIG. 5 articulated to a limit position.

A first embodiment of prosthesis of the invention, indicated generally, by the numeral 28 in FIGS. 5 and 6, includes a pair of identical prosthesis plates 10 arranged in opposition to one another. The prosthesis 28 also includes a core 30 illustrated in FIGS. 3 and 4. The core is made in one piece of a low friction plastics material, in this case a polyethylene known as Orthosol, but a variety of other high molecular weight polyethylenes might also find use. Alternatively, the core could be composed of a metal, such as cobalt chrome, or of a ceramic. The core is generally in the form of a circular, doughnut-shaped toroid and has identical upper and lower surfaces 32 which are convexly, spherically curved. The upper and lower surfaces 32 are formed centrally with conical openings 34, in this case forming the opposite ends of a circular cross-section passage 36 passing axially and centrally through the body of the core.

The core surfaces 32 and recess surface 26 have the same radius of curvature which is, in this case, 18 mm.

In the assembled prosthesis 28, the plates 10 are arranged in opposition to one another with the core 30 located between them. The pegs 22 of the plates locate in the openings 34, i.e. in the ends of the passage 36. The combined length of the pegs is less than the length of the passage 36, so the inner ends of the pegs are spaced apart from one another by a short distance 38, as shown in FIG. 5. The transverse dimension of each peg is, at all points along the length of the peg, considerably less than the diameter of the passage 36 at the corresponding point along the length of the passage.

The cooperating spherical surfaces 26 and 32 and the relative dimensions of the pegs 22 and the passage 36 allow the plates 10 to slide or articulate over the core through a fairly large range of angles and in all directions or degrees of freedom, including rotation about the central axis.

At a predetermined limit of articulated movement of the plates relative to the core, the rims 24 of the plates contact with one another as indicated by the numeral 40 in FIG. 6. Further articulation of the prosthesis 28 beyond this point is not possible. At the limit of articulation, the pegs 22 also come into abutment with the side of the passage 36, as also illustrated in FIG. 6.

It will also be noted in FIG. 6 that the openings 34 at the ends of the passage 36 are defined by similar cone angles to the pegs 22, so that contact between the pegs and the sides of the openings takes place complementally over virtually the entire length of each peg.

Throughout the range of possible articulation, the pegs 22 remain in the passage 36 and prevent the core from separating laterally from the plates 10. In other words, the core is held captive by the pegs during all possible articulations which can take place. In the illustrated embodiment, the plates 10 are limited to 12° of articulation before the rims 24 abut one another, i.e. 12° is the maximum articulation which can take place.

In the prosthesis 28 described above, the pegs 22 locate in a passage 32 which passes right through the core 30. It will however be understood that in other embodiments, the pegs could merely locate in blind recesses or openings in the opposite surfaces of the core without such openings actually being joined to one another to form a continuous passage.

Figure 7:
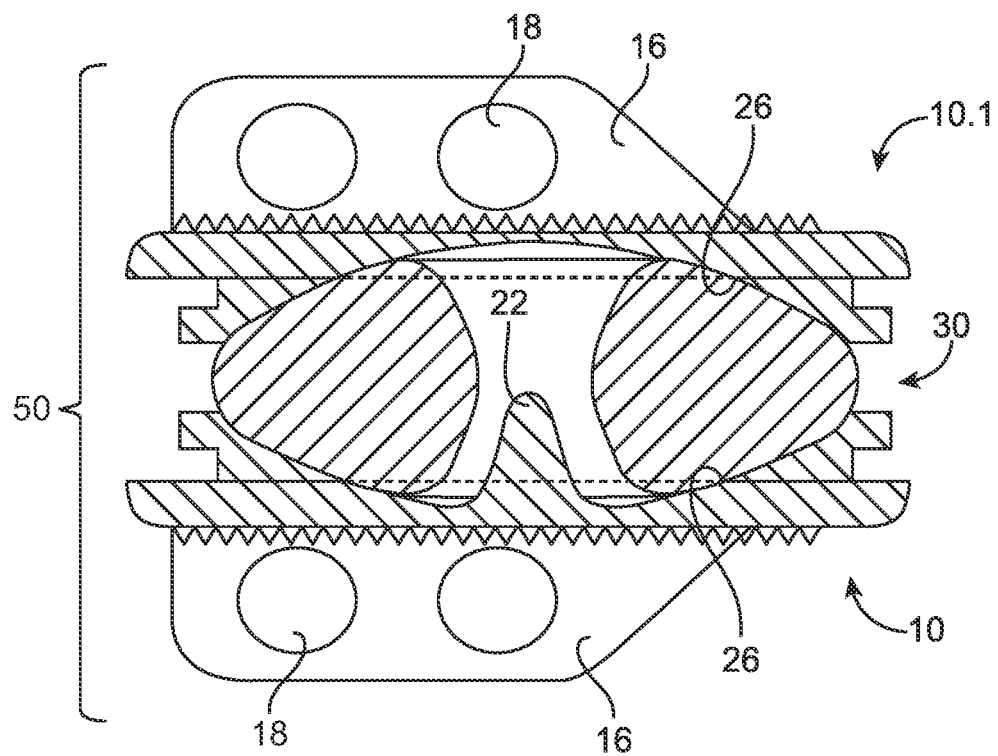
FIG. 7 shows a cross-sectional view of an intervertebral prosthesis according to a second embodiment of the invention.

FIG. 7 illustrates a prosthesis according to a second embodiment of the invention in a view similar to that of FIG. 5. In FIG. 7, components corresponding to components illustrated in the earlier Figures are indicated by the same reference numerals.

The lower prosthesis plate 10 in FIG. 7 is identical to the prosthesis plates of the first embodiment. However, the upper prosthesis plate, designated 10.1, has no central peg. Instead, the surface 26 is continuously, spherically curved. In all other respects the plate 10.1 is identical to the plate 10.

Figure 8:
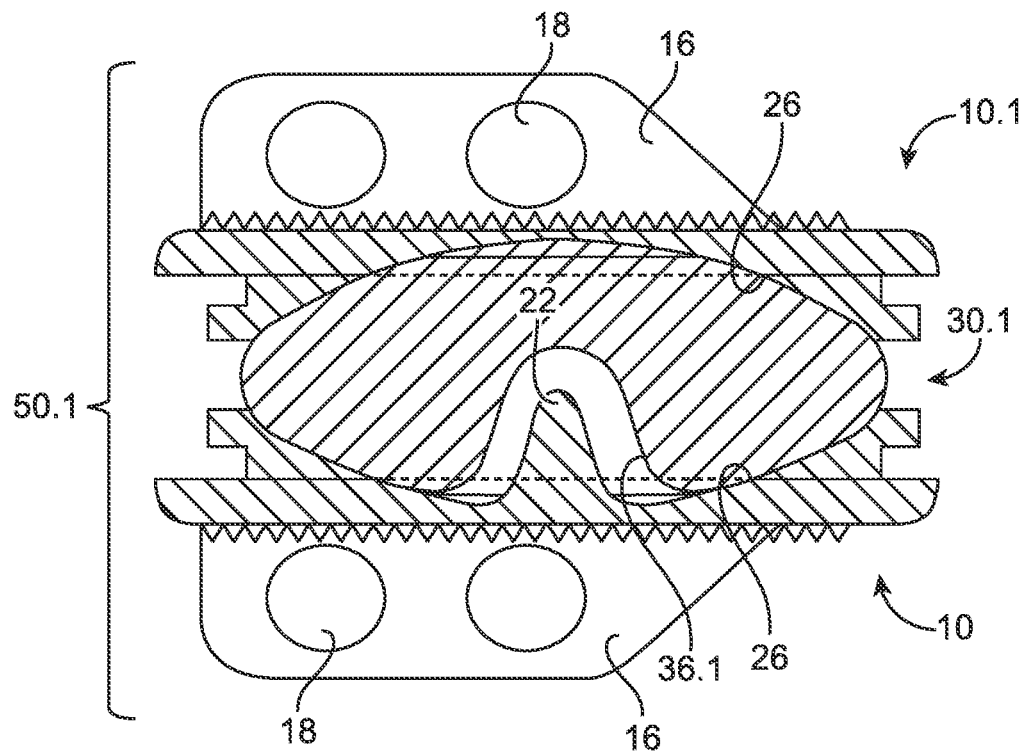
FIG. 8 shows a cross-section intervertebral prosthesis according to a third embodiment of the invention.

In the assembled prosthesis 50, the core is held captive by the action of the single peg 22 carried by the lower prosthesis plate 10. The core 30 is identical to the core described previously but once again it will be appreciated that core could have a blind recess in its downwardly facing, curved surface 32 only to receive the single peg 22. In the assembled prosthesis 50.1 of FIG. 8, the core 30.1 has a blind recess 36.1 in its downwardly facing, curved surface only to receive the single peg 22.

The prosthesis 28, 50 is surgically implanted between adjacent spinal vertebrae in place of a damaged disc. Those skilled in the art will understand that the adjacent vertebrae are forcibly separated from one another to provide the necessary space for insertion. The plates 10, 10.1 are slipped laterally into place between the vertebrae with their fins 16 entering slots cut in the opposing vertebral surfaces to receive them.

After insertion of the core between the opposing plates, the vertebra are allowed to move together to hold the assembled prosthesis in place.

The surfaces 12 of the plates 10, 10.1 locate against the opposing vertebrae and, with passage of time, firm connection between the plates and the vertebrae will be achieved as bone tissue grows over the serrated finish. Bone tissue growth will also take place about the fins 16 and through the holes 18 therein, further enhancing the connection which is achieved.

Figure 3:
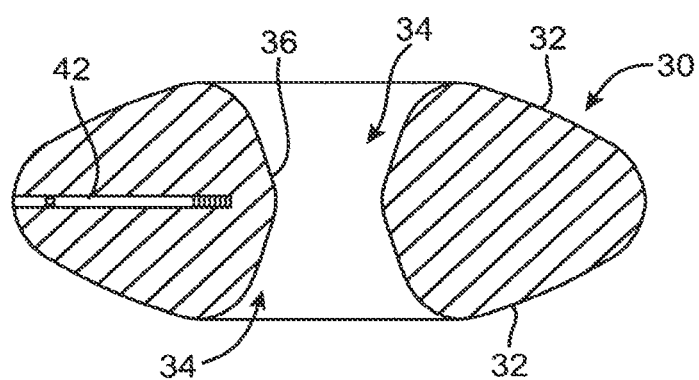
FIG. 3 shows a cross-sectional view of a core used in a prosthesis according to the invention.

Referring to FIGS. 3 and 4, the core 30 used in the embodiments described above is formed with narrow, angularly spaced, blind passages which accommodate titanium pins 42. The core itself is transparent to X-radiation and so would normally be invisible in a post-operative X-rays examination. The pins 42 serve as radiographic markers and enable the position of the core 30 to be ascertained during such examination.

Annular grooves 44 are provided in the plates 10, 10.1 to facilitate holding and manipulation of the prosthesis by appropriate instruments during placement into the intervertebral disc space.

Compared to known prostheses, the prostheses 28, 50 described above have a number of advantages, as follows:

1. The peg or pegs 22 hold the core captive and prevent it from slipping out sideways.

2. At a predetermined maximum limit of articulation, the rims 24 contact one another to prevent further articulation. At the same time, the peg or pegs 22 contact the sides of the openings 34, also preventing further articulation.

3. An acceptable bearing area of the plates on the core is obtained with the central peg/central opening configurations described above. This is particularly advantageous compared to prior art prostheses where the core has peripheral channels on its upper and lower surfaces to receive peripheral rims on the plates at the limit of articulation.

In practice, it may happen that there is imperfect alignment of the prosthesis plates. In the case of very poor alignment, the dual peg configuration of FIGS. 5 and 6 gives rise to the possibility that the pegs 22 are laterally offset from one another by a substantial distance. This can in turn lead to the undesirable consequence that the range of articulation which can be accommodated is unduly limited, and attempts to articulate past the limit could result in damage to the core by the misaligned pegs. In the embodiment of FIG. 7 the single peg can be received centrally by the core, thereby avoiding this potential problem.

The principles of the invention are applicable to prosthetic disc implants for lumbar vertebrae as well as cervical vertebrae. In the latter case, the fins 16 will typically be omitted.

What is claimed is:

1. A method of inserting an intervertebral prosthesis in an intervertebral space, the method comprising:
    providing an articulating intervertebral prosthesis including:
        a first prosthesis plate having a major surface to engage a first vertebra and a cooperating surface disposed opposite the major surface;
        a second prosthesis plate comprising a major surface to engage a second vertebra and a cooperating surface disposed opposite the major surface;
        a core located between the first and second prosthesis plates, wherein the cooperating surfaces of the first and second prosthesis plates are arranged to cooperate with the core to form an articulate joint;
        a peg projecting centrally from the cooperating surface of the first prosthesis plate and a central opening in the core, wherein the peg locates loosely in the opening of the core, whereby the plates can slide over the core while the peg holds the core captive;
        wherein the core includes at least one continuously curved bearing surface;
        a first annular rim disposed around the cooperating surface of the first prosthesis plate, the first rim having an empty groove formed adjacent to the first rim;
        a second annular rim disposed around the cooperating surface of the second prosthesis plate, the second rim having an empty groove formed adjacent to the second rim; and
        each groove configured and arranged to facilitate handling of the plates by instruments used to place the prosthesis in use; and
    manipulating the prosthesis with an instrument to place the prosthesis in entirely within the intervertebral space;
    wherein the grooves facilitate manipulation and holding of the prosthesis while the prosthesis is placed in the intervertebral space.

2. The method according to claim 1, wherein the first and second prosthesis plates are secured to vertebrae adjacent the intervertebral space by elongated protrusions extending from the major surfaces of the first and second prosthesis plates.

3. The method according to claim 1, wherein the second prosthesis plate does not include a central projecting peg.

4. The method according to claim 1, further comprising contacting the second annular rim with the first annular rim to prevent further articulation.

5. The method according to claim 1, further comprising contacting the core with the peg to prevent further articulation of the first and second prosthesis plates over the core.

6. The method according to claim 1, wherein only a lower plate of the first prosthesis plate and the second prosthesis plate includes the peg.

7. The method according to claim 1, wherein the central opening in the core is a blind recess extending partway through the core.

8. The method according to claim 1, further comprising causing the cooperating surface of the first prosthesis plate to complementarily engage a curved surface of the core of the prosthesis.

9. The method according to claim 1, wherein the first and second prosthesis plates are formed of titanium.

10. The method according to claim 1, wherein the core is formed of high molecular weight polyethylene.

11. A method of inserting an intervertebral prosthesis in an intervertebral space, the method comprising:
    providing an articulating intervertebral prosthesis including:
        a first prosthesis plate having a major surface to engage a first vertebra and a cooperating surface disposed opposite the major surface;
        a second prosthesis plate comprising a major surface to engage a second vertebra and a cooperating surface disposed opposite the major surface,
        a core located between the first and second prosthesis plates, wherein the cooperating surfaces of the first and second prosthesis plates are arranged to cooperate with the core to form an articulate joint;
        a peg projecting centrally from the cooperating surface of the first prosthesis plate and a central opening in the core, wherein the peg locates loosely in the opening of the core, whereby the plates can slide over the core while the peg holds the core captive and wherein the second prosthesis plate does not include a central projecting peg;
        wherein the core includes at least one continuously curved bearing surface;
        a first annular rim disposed around the cooperating surface of the first prosthesis plate, the first rim having an empty groove formed adjacent to the first rim;
        a second annular rim disposed around the cooperating surface of the second prosthesis plate, the second rim having an empty groove formed adjacent to the second rim; and
        each groove configured and arranged to facilitate handling of the plates by instruments used to place the prosthesis in use; and manipulating the prosthesis with an instrument to place the prosthesis in entirely within the intervertebral space;
wherein the grooves facilitate manipulation and holding of the prosthesis while the prosthesis is placed in the intervertebral space.

12. The method according to claim 11, wherein the first and second prosthesis plates are secured to vertebrae adjacent the intervertebral space by elongated protrusions extending from the major surfaces of the first and second prosthesis plates.

13. The method according to claim 11, further comprising contacting the second annular rim with the first annular rim to prevent further articulation.

14. The method according to claim 11, further comprising contacting the core with the peg to prevent further articulation of the first and second prosthesis plates over the core.

15. The method according to claim 11, further comprising causing the cooperating surface of the first prosthesis plate to complementarily engage a curved surface of the core of the prosthesis.

16. A method of inserting an intervertebral prosthesis in an intervertebral space, the method comprising:
providing an articulating intervertebral prosthesis including:
a first prosthesis plate having a major surface to engage a first vertebra and a cooperating surface disposed opposite the major surface;
a second prosthesis plate comprising a major surface to engage a second vertebra and a cooperating surface disposed opposite the major surface;
a core located between the first and second prosthesis plates, wherein the cooperating surfaces of the first and second prosthesis plates are arranged to cooperate with the core to form an articulate joint;
a peg projecting centrally from the cooperating surface of the first prosthesis plate and a central opening in the core, wherein the peg locates loosely in the opening of the core, whereby the plates can slide over the core while the peg holds the core captive;
wherein the core includes at least one continuously curved bearing surface;
a first annular rim disposed around the cooperating surface of the first prosthesis plate, the first rim having an empty groove formed adjacent to the first rim;
a second annular rim disposed around the cooperating surface of the second prosthesis plate, the second rim having an empty groove formed adjacent to the second rim; and
each groove configured and arranged to facilitate handling of the plates by instruments used to place the prosthesis in use;
manipulating the prosthesis with an instrument to place the prosthesis in entirely within the intervertebral space;
contacting the second annular rim with the first annular rim to prevent further articulation; and
contacting the core with the peg to prevent further articulation of the first and second prosthesis plates over the core;
wherein the grooves facilitate manipulation and holding of the prosthesis while the prosthesis is placed in the intervertebral space.

17. The method according to claim 16, wherein the first and second prosthesis plates are secured to vertebrae adjacent the intervertebral space by elongated protrusions extending from the major surfaces of the first and second prosthesis plates.

18. The method according to claim 16, wherein the second prosthesis plate does not include a central projecting peg.

19. The method according to claim 16, wherein only a lower plate of the first prosthesis plate and the second prosthesis plate includes the peg.

20. The method according to claim 16, wherein the central opening in the core is a blind recess extending partway through the core.

* * * * *